United States Patent [19]
Alchas et al.

[11] Patent Number: 5,441,539
[45] Date of Patent: Aug. 15, 1995

[54] ENDOTHELIAL CELL DEPOSITION DEVICE

[75] Inventors: Paul G. Alchas, Wayne; Jonathan B. Gabel, Clifton, both of N.J.; Stuart K. Williams, Wilmington, Del.; Bruce E. Jarrell, Philadelphia, Pa.; Deborah G. Rose, Warrington, Pa.; Pauline K. Park, Philadelphia, Pa.; Thomas L. Carter, Philadelphia, Pa.; Frank A. Augello, Cedar Knolls, N.J.; Joseph A. DiPisa, Jr., Wyckoff, N.J.

[73] Assignees: Thomas Jefferson University, Philadelphia, Pa.; Becton Dickinson and Company, Franklin Lakes, N.J.

[21] Appl. No.: 96,216

[22] Filed: Jul. 22, 1993

Related U.S. Application Data

[60] Continuation of Ser. No. 763,875, Sep. 20, 1991, abandoned, which is a continuation of Ser. No. 485,298, Feb. 26, 1990, abandoned, which is a continuation-in-part of Ser. No. 356,431, May 24, 1989, Pat. No. 5,035,708, which is a continuation-in-part of Ser. No. 244,496, Sep. 12, 1988, abandoned, which is a division of Ser. No. 742,086, Jun. 6, 1985, Pat. No. 4,820,626.

[51] Int. Cl.⁶ ............................. A61F 2/06; A01N 1/02
[52] U.S. Cl. ........................................ 623/66; 435/1; 623/1; 623/11
[58] Field of Search ............... 623/1, 12, 66; 600/36; 604/35, 48, 319, 902; 435/1, 240.1, 240.21, 240.23

[56] References Cited

U.S. PATENT DOCUMENTS

| | | | |
|---|---|---|---|
| 4,014,329 | 3/1977 | Welch et al. | 604/4 |
| 4,418,693 | 12/1983 | LeVeen et al. | 623/1 X |
| 4,503,569 | 3/1985 | Dotter | 606/195 |
| 4,546,500 | 10/1985 | Bell | 623/1 |

FOREIGN PATENT DOCUMENTS

| | | | |
|---|---|---|---|
| 0281736 | 9/1988 | European Pat. Off. | |
| 0320441 | 6/1989 | European Pat. Off. | |
| 2815614 | 10/1978 | Germany | 623/1 |

OTHER PUBLICATIONS

Jarrell et al. "Human Endothelial Cell Growth in Culture" Journal of Vascular Surgery, vol. 1, No. 6, pp. 757–764 Nov., 1984.

Herring et al. "A Single and Staged Technique for Seeding Vascular Grafts with Autogenous Endothelium" Surgery, 1978 84:498–504.

Graham et al. "Cultured Autogenous Endothelial Cell Seeding of Vascular Prosthetic Grafts" Surg Forum 30:204–206 (1979).

Graham et al. "Expanded Polytetrafluoroethylene Vascular Prostheses Seeded with Enzymatically Derived and Cultured Canine Endothelial Cells" Surgery 91:550–559 (1982).

Dilley et al. "Endothelial Seeding of Vascular Prostheses" Jaffe ed. Biology of Endothelial Cells, the Hague: Martinus Nijhoff, 1984 pp. 401–411.

Berger et al. "Healing of Arterial Prostheses in Man It's Completeness" Ann. Surg 175:118–127 (1972).

(List continued on next page.)

*Primary Examiner*—David Isabella
*Attorney, Agent, or Firm*—Woodcock, Washburn, Kurtz, Mackiewicz & Norris

[57] ABSTRACT

Apparatus for depositing a cell product, such as endothelial cell product, in a graft and inserting the graft in a vessel is disclosed. The apparatus preferably comprises a tunneler tube that has a hollow portion for supporting the graft therein, apertures to permit the flow of cell product, and a pointed end cap attached to a distal end of the tunneler tube. The apparatus also has a handle connected to the graft and releaseably connected to a proximal end of the tunneler tube that provides an inlet for cell product and outlet in fluid communication with the lumen of the graft. During deposition, the cell product thus flows through the handle, into the graft and exits through the apertures. During insertion, the tunneler tube is manipulated by the handle to enter a vessel, and is then released from the handle and removed to accommodate anastomoses.

10 Claims, 12 Drawing Sheets

OTHER PUBLICATIONS

Jaffe et al. "Synthesis of Antihemophilia Factor Antigen by Cultured Human Endothelial Cells" J. Clin. Invest. 55:2757-64 (1973).

Lewis "Endothelium in Tissue Culter" Am. J. Anat. 30:39-59 (1922).

Jaffe et al. "Culture of Human Endothelial Cells Derived from Umbilical Veins" J. Clin. Invest. 52:2745-56 (1973).

Baker et al., "Endothelialization of Human Collagen Surface with Human Adult Endothelial Cells", American Journal of Surgery, 150:197-200 (Aug., 1985).

Williams et al., "Isolation and Culture of Phenotypically Diverse Human Perinecphric Fat Capillary Endothelium", Microvascular Research. 20:250 (1985).

Jarrell et al., "Use of Freshly Isolated Capillary Endothelial Cells for the Immediate Establishment of a Monolayer or a Vascular Graft at Surgery".

Radomski et al., "Initial Adherence of Human Capillary Endothelial Cells to Dacron", (Abstract).

Abedin, M. Z. et al. "Collagen Heterogeneity and Its Functional Significance" Die Angewandte Markromolekulare Chemie, vol. 111, No. 1701 Jan. 1983, pp. 107-222.

Kern et al. "Isolation and Culture of Microvascular Endothelium from Human Adipose Tissue" J. Clin. Invest. 71:1822-1829 (Jun. 1983).

Van Wachem et al. "Interaction of Cultured Human Endothelial Cells with Polymeric Surfaces of Different Wettabilities" Bimaterials 6:403-408 (1985).

Azizkham et al. "Mast Cell Heparin Stimulates Migration of Capillary Endothelial Cells in Vitro" J. Exp. Med. vol. 152 Oct. 1980 pp. 931-944.

Roblin et al. "Cell Surface Changes Correlated with Density Dependent Growth Inhibition: Glycosaminoglycan Metabolism in 3T3, SV3T3, and Con A Selected Revertant Cells" Biochemistry vol. 14, No. 2 1975 pp. 347-357.

Yang et al. "The Effect of Heparin on Growth of Mammalian Cells in Vitro" (40290) Proceedings of the Soc. for Experimental Biology and Medicine 159:88-93 (1978).

Thornton et al. "Human Endothelial Cells: Use of Heparin in Cloning and Long-Term Serial Cultivation" Science 11 Nov. 1983, vol. 222, pp. 623-625.

Laterra et al. "Functions for Fibronectin, Hyaluronate and Heparin Proteoglycans in Substratum Adhesion of Fibroblasts" Extracellular Matrix pp. 197-207, 1982.

Maciaq et al., "Factors Which Stimulate the Growth of Human Umbilical Vein Endothelial Cells in Vitro", Jaffe, E. A. (ed.) Biology of endothelial cells. 1984 Martinus Nijohff, pp. 87-140.

Madri, "The Immunochemistry of Extracellular Matrix", Boca Raton, Fla., CRC Press, (1982), vol. 1:75-90.

Wagner et al. "Exclusion of Albumin from Vesicular Ingestion by Isolated Microvessels" Microvascular Research 19:127-130 (1980).

Williams et al. "Metabolic Studies on the Micropinocytic Process in Endothelial Cells" Microvascular Research 18:175-184 (1979).

Williams "Vesicular Transport of Proteins by Capillary Endothelium" Annals of the New York Acadamy of Sciences 457-467 (1983).

Williams et al. "Enhanced Vesicular Ingestion of Nonenzymatically Glucosylated Proteins by Capillary Endothelium" Microvascular Research 28:311-321 (1984).

Williams et al. "Endocytosis and Exocytosis of Protein in Capillary Endothelium" Journal of Cellular Physiology 120:157-162 (1984).

Williams et al. "Isolation and Characterization of Brain Endothelial Cells: Morphology and Enzyme Activity" Journal of Neurochemistry 35:374-381.

McDonagh et al. "The Preparation and Use of Fluorescent-Protein Conjugates for Microvascular Research" Microvascular Research 27:14-27 (1984).

Madri et al. "Capillary Endothelial Cell Cultures: Phenotypic Modulation by Matrix Components" Journal of Cell Biology vol. 97, Jul. 1983 pp. 153-165.

Williams et al. "Adult Human Endothelial Cell Compatability with Prosthetic Graft Material" Journal of Surgical Research 38:618-629 (1985).

S. G. Eskin et al. "Behavior of Endothelial Cells Cultured on Silastic and Dacron Velour Under Flow Conditions In Vitro Implications for Prelining Vascular Grafts with Cells" Artificial Organs 7(1):31-37 (1983).

T. A. Belden et al. "Endothelial Cell Seeding of Small-Diameter Vascular Grafts" Trans. Am. Soc. Artif. Intern. Organs 28:173-177 (1982).

(List continued on next page.)

OTHER PUBLICATIONS

W. E. Burkel et al. "Fate of Knitted Dacron Velour Vascular Grafts Seeded With Enzymatically Derived Autologous Canine Endothelium" Trans. Am. Soc. Artif. Intern. Organs 2:178–82 (1982).

Herring et al. "Seeding Arterial Prostheses With Vascular Endothelium" Ann. Surg. vol. 190, No. 1, pp. 84–90 (Jul. 1979).

A. Wesolow "The Healing of Arterial Prostheses: The State of the Art" Thorac. Cardiovasc. Surgeon 30:196–208 (1982).

T. Ishihara et al. "Occurrence and Significance of Endethelial Cells in Implanted Procine Bioprosthetic Valves" American Journal of Cardiology 48:443–454 (Sep. 1981).

Williams et al. "Micropinocytic Ingestion of Glycosylated Albumin by Isolated Microvessels: Possible Role in Pathogenesis of Diabetic Microangiopathy" Proc. Natl. Acad. Sci. USA vol. 78, No. 4, pp. 2393–2397 Apr. 1981.

Williams et al. "Regulation of Micropinocytosis in Capillary Endothelium by Multivalent Cations" Microvascular Research 21 175–182 (1981).

Williams et al. "Quantitative Determination of Deoxyribonuclein Deoxyribonuclein Acid from Cells Collected on Filters" Analytical Biochemistry 107:17–20 (1980).

Glassberg et al. "Cultured Endothelial Cells Derived From Human Iliac Arteries" in Virtro 18:859–866 (1982).

Sharefkin et al. "Early Normilization of Platelet Survival by Endothelial Seeding of Dacron Arterial Prostheses in Dogs" Surgery 92:385–393 (1982).

Stanely et al. "Enhanced Patency of Small Diameter Externally Supported Dacron Iliofemoral Grafts Seeded with Endothelial Cells" Surgery 92:994–1005 (1982).

Watkins et al. "Adult Human Saphenous Vein Endothelial Seeding of Vascular Prosthese" J. Surg. Res. 36:588–596 (1984).

Fishman "Endothelium: A Distributed Organ of Diverse Capabilities" Annals of New York Academy of Sciences, pp. 1–8 (1982).

Sauvage et al. "Interspecies Healing of Porous Arterial Prostheses" Arch Surg. 109:698–705 (1974).

F. Hess et al. "The Endothelialization Process of a Fibrous Polyurethane Microvascular prostheses After Implantation In The Abdominal Aorta of the Rat" Journal of Cardiovascular Surgery, vol. 24, No. 5, pp. 516–524 (Sep.–Oct. 1983).

W. K. Nicholas et al. "Increased Adherence fo Vascular Endothelial Cells to Biomer Precoated With Extracellular Matrix" Trans. Am. Soc, Artif. Intern. Organs 28:208–212 (1981).

C. L. Ives et al. "The Improtance of Cell Origin and Substrate in the Kinetics of Endothelial Cell Alignment in Response to Steady Flow" Trans. Am. Soc, Artif Intern. Organs 29:269–274 (1983).

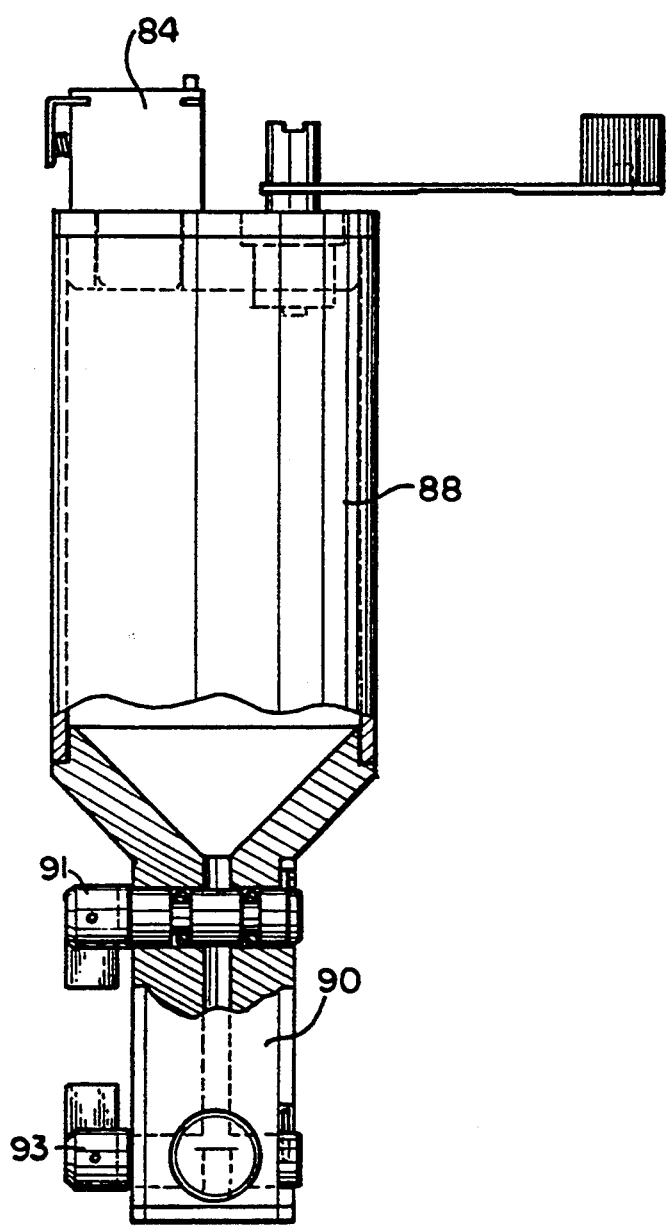
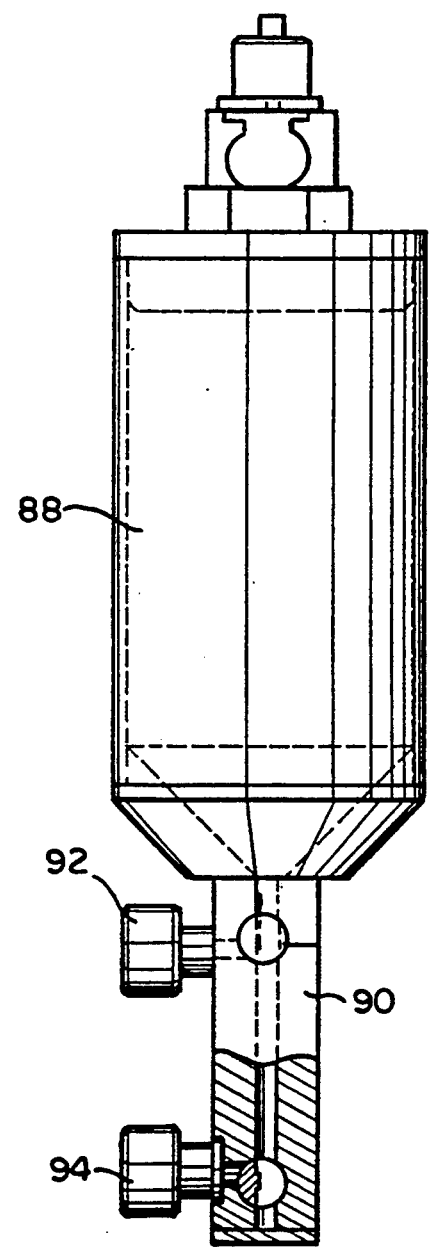
FIG. 7a
FIG. 7b

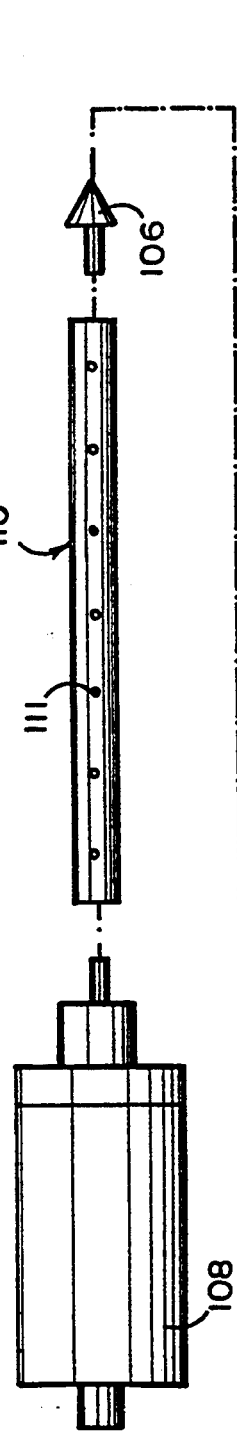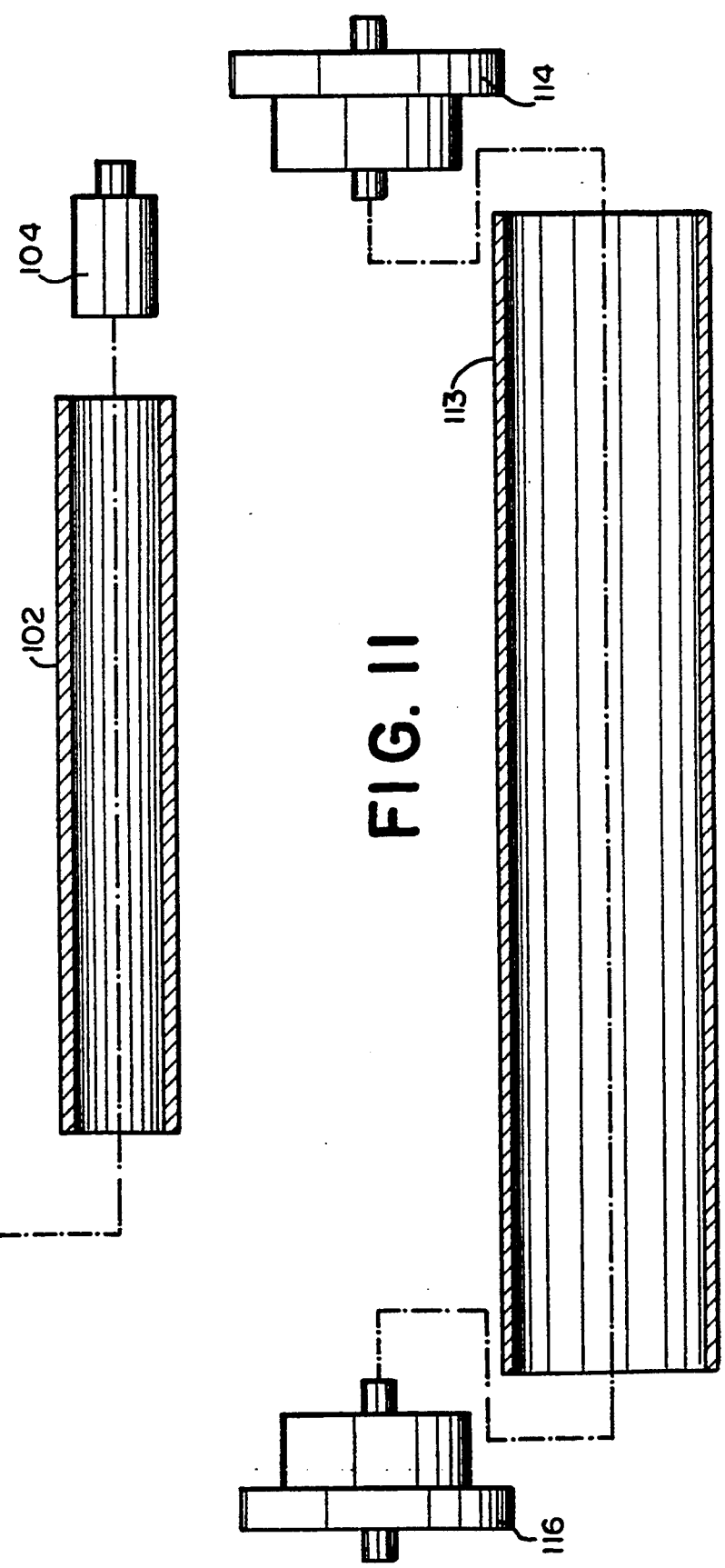

ENDOTHELIAL CELL DEPOSITION DEVICE

CROSS-REFERENCE TO RELATED APPLICATIONS

This application is a continuation of application Ser. No. 07/763,875 filed Sep. 20, 1991 now abandoned; which is a continuation of prior application Ser. No. 07/485,298, filed on Feb. 26, 1990, abandoned, which a continuation-in-part of application Ser. No. 356,431, filed May 24, 1989, in the names of Paul G. Alchas, Frank A. Augelio, Christopher J. Brooks, Tony A. Cutshall, Joseph A. DiPisa, Jr., Stuart K. Williams, Jonathan B. Gabel, Paul J. Mulhauser, Wes Prais, Bruce E. Jarrell and Deborah G. Rose entitled "Endothelial Cell Procurement and Deposition Kit" which is a continuation-in-part of application Ser. No. 244,496, filed Sep. 12, 1988, now abandoned in the names of Stuart K. Williams and Bruce E. Jarrell entitled "A Method of Treating a Synthetic or Naturally Occurring Surface with Microvascular Endothelial Cells and the Treated Surface Itself", which is a division of application Ser. No. 742,086, filed Jun. 6, 1985 and issued Apr. 11, 1989 as U.S. Pat. No. 4,820,626 in the names of Stuart K. Williams and Bruce E. Jarrell entitled "Method of Treating a Synthetic or Naturally Occurring Surface with Microvascular Endothelial Cells, and the Treated Surface Itself", each of which prior applications is assigned in whole or in part to Thomas Jefferson University, which is a co-assignee with Becton Dickinson and Company of the present application, which applications are hereby incorporated by reference.

This application is related to copending applications Ser. No. 927,745, filed Nov. 6, 1986, now abandoned entitled "Method of Determining Endothelial Cell Coverage of a Prosthetic Surface"; Ser. No. 848,453, filed Apr. 4, 1986, now abandoned entitled "A Method of Treating a Synthetic or Naturally Occurring Surface with Collagen Laminate to Support Microvascular Endothelial Cell Growth and the Surface Itself"; Ser. No. 114,242, filed Oct. 28, 1987 entitled "Method of Reendothelializing Vascular Linings", all of which are continuation-in-parts of parent application Ser. No. 742,086, now U.S. Pat. No. 4,820,626 each of which applications is assigned to Thomas Jefferson University, which applications are hereby incorporated by reference.

BACKGROUND OF THE INVENTION

While autologous vein remains the graft of choice, advanced vascular disease and prior surgical intervention limit the availability of autologous grafts. The use of synthetic grafts provides a means for restoring blood flow to ischemic areas when no alternative is available. Over the past three decades, artificial grafts have been used to provide immediate restoration of blood flow to areas of ischemia as a result of atherosclerotic vascular disease. In addition, they have been used to provide vascular access for hemodialysis in patients with chronic renal failure, and in the repair of arterial aneurysms. Although initially successful in restoring perfusion to ischemic tissues, the long term prognosis for these grafts is not encouraging. Commercially available grafts are far from ideal due to their inherent thrombogenicity. Over an extended period of time, grafts less than 4 mm in diameter lose their patency as they become occluded via fibrin deposition and cellular adhesion. This process appears to be secondary, and to be due in part to the thrombogenic nature of the nude, i.e., nonendothelialized, surface of an implanted prosthesis. See Berger et al., "Healing of Arterial Prostheses in Man: It's Incompleteness", Ann. Surg. 175: 118–27 (1972). Thus, much current research is being focused on lining prostheses with human endothelial cells, in the hope of producing a non-thrombogenic endothelial cell surface such as exists in native human vessels. In dogs, seeding of endothelial cells onto both small and large diameter grafts have been shown to result in a complete endothelial cell lining in between 1–4 months. Since vascular endothelium is said to represent a unique non-thrombogenic surface, endothelial cells are reported to be "the first logical choice for lining small diameter vascular grafts". The transplantation of a functional endothelial cell lining onto the surface of a vascular graft has proven to increase patency rates and decrease thrombus formation on the flow surface in animal models. Past and present studies have focused on the isolation of large vessel endothelial cells from vein segments, with the subsequent seeding of these cells on the graft lumenal surface. Tissue culture advances have also made the generation of large numbers of endothelial cells for high-density seeding on vascular prosthesis possible. These techniques have major drawbacks in the clinical setting. Endothelialization occurs at a slow rate when low density seeding techniques are applied. High-density seeding, using cultured endothelial cells requires the use of undefined media, not easily applicable to the clinical setting.

It has been recognized that human microvascular endothelial cells i.e., the cells which are derived from capillaries, arterioles, and venules, will function suitably in place of large vessel cells even though there are morphological and functional differences between large vessel endothelial cells and microvessel endothelial cells in their native tissues. Microvascular endothelial cells are present in an abundant supply in body tissue, most notably in fat tissue, and may be used to establish a degree of preimplantation confluence, i.e., at least 50%, which should dramatically improve the prognosis of most implants. For purposes of further description, fat tissue is designated as the exemplary source of microvascular endothelial cells, but it is recognized that endothelial cells from other tissues may be used as well.

To overcome the problems associated with seeding large vessel endothelial cells on prosthetic grafts, methods for the isolation of microvessel endothelial cells from autologous adipose tissue followed by high density seeding of a vascular prosthesis were developed.

Although microvessel endothelial cells have been shown to be capable of endothelializing a blood-contacting surface, methods of procuring and depositing these cells in an operating room setting present special considerations. A vascular graft or other implant is treated to confluence using microvascular endothelial cells which are separated from fat which is obtained at the beginning of an uninterrupted surgical procedure. Fat tissue is removed from the patient after sterile conditions have been established. Microvascular endothelial cells in that fat are then quickly separated from their related tissue by enzymatic digestion and centrifugation, and are used to treat a surface which is then implanted in the patient during the latter stages of the same operation. This procedure permits a patient to receive a graft which has been treated up to or above confluence with his own fresh endothelial cells.

The microvascular rich tissue obtained is perinephric fat, subcutaneous fat, omentum, or fat associated with the thoracic or peritoneal cavity. This tissue is then subjected to digestion using a proteolytic enzyme such as collagenase, comprising caseanase and trypsin, which is incubated with the tissue until the tissue mass disperses to produce a tissue digest. The microvascular endothelial cells are then separated from the digest using low speed centrifugation to produce an endothelial cell rich pellet. The pellet is washed with a buffered saline solution. The resulting microvascular endothelial cells are then preferably suspended in a buffered saline solution containing plasma protein, preferably about 1% plasma protein. This suspension, which comprises, on a volumetric basis, a pellet to solution ratio of 1:5 to 1:15, or preferably about 1:10, is then used to treat the surface by incubating cells with that surface until sufficient adherence of the microvascular endothelial cells to that surface occurs to provide at least 50% confluence. As a result, an improved graft implant is provided having endothelialized surfaces which are either confluent, or which reach confluence quite rapidly (within one population doubling) following implantation.

Implants which can be treated to produce such an endothelial cell lining include but are not limited to, for example, intravascular devices such as artificial vascular prostheses, artificial hearts, and heart valves. The herein disclosed kit and methods for endothelializing surfaces can be used for surfaces composed of known synthetic materials such as polyester, polytetrafluoroethylene, or naturally occurring materials, such as umbilical vein, saphenous vein, and native bovine artery.

Methods currently used employ standard laboratory equipment such as beakers, flasks, centrifuge tubes, shaker baths, pipettes, syringes, sterile hoods. In the method disclosed by Jarrell and Williams, the donated tissue is immediately transferred to ice cold buffered saline (pH 7.4) wherein the buffering agent is preferably a phosphate, i.e., a phosphate buffered saline (PBS). The tissue is minced with fine scissors and the buffer decanted. The proteolytic enzyme collagenase, containing caseanase and trypsin, is added to the tissue and incubated at 37 degrees C. until the tissue mass disperses. The digestion occurs within 30 minutes and generally should be less than 20 minutes. The digest is transferred to a sterile test tube and centrifuged at low speed ($700 \times g$) in a table top centrifuge for 5 minutes at room temperature. The pellet of cells thus formed consists of greater than 95% endothelial cells. These endothelial cells are described herein as microvascular endothelial cells (MEC) since they originate from the arterioles, capillaries and venules, all elements of the microvasculature. The MEC pellet is washed 1 time by centrifugation with buffered saline, preferably PBS. The MEC suspension is then preferably pelletized by centrifugation ($200 \times g$) and the pellet resuspended with protein containing buffer solution. This resuspension should be performed at a ratio of approximately 1:5 to 1:15 or about 1:10 volumes of packed microvascular endothelial cells to buffer solution. The cell suspension is added to tubular grafts and the ends clamped, or the cells layered upon the surface to be treated. Optimum periods for cell interaction vary upon the material of the prosthesis, the nature of any pretreatments it may have received and whether the surface of the prosthesis has been modified to improve its acceptance of the MEC. Following incubation for a sufficient time to permit adherence of the endothelial cells with the prosthesis surface, the surface is washed with a protein containing buffer. The prosthesis is then implanted in its normal manner. In Williams' and Jarrell's U.S. Pat. No. 4,820,626 and related applications, methods of treating a graft surface with endothelial cells are disclosed. According to those methods, subcutaneous adipose tissue is aspirated via a cannula and transferred by vacuum into a mucous trap. The trap is then transferred to a sterile hood for further processing. Adipose tissue is transferred to a sieve inside a funnel which is placed in a sterile beaker. A rinsing solution is then poured over the tissue to remove red blood cells and lysed fat. The tissue is manually poured into a sterile Erlenmeyer flask containing collagenase solution and agitated at 37° C. for 20 minutes. The collagenase slurry is manually poured into sterile conical centrifuge tubes and spun for seven minutes at $700 \times 6$. The endothelial cells are then pipetted out of the tube. A graft is tied to a male luer extension and secured within a tube. The cells are resuspended in serum protein media and drawn into a syringe. Using a needle and a syringe, the cells are forced into the lumen of the graft. The graft is manually rotated for 2 hours.

In spite of these advances, a need still exists for a simple, reliable method of producing endothelial cell coatings on a graft in an operating room setting. The present invention provides for the isolation of large quantities of endothelial cells which can be readily performed in an operating room. While endothelial cells can be isolated from tissues other than fat, such as brain, lung, retina, adrenal glands, liver and muscle, the use of fat tissue as the source of the cells is preferred due to its abundance and availability, and due to the fact that its removal should not adversely affect the patient being treated. Although less preferred, it is possible to obtain human perinephric fat from brain-dead but heart beating cadaver donors, or from donors other than the patient during the donor's surgery. The isolated endothelial cells are then deposited on a graft for implantation.

SUMMARY OF THE INVENTION

The present invention provides a simple, reliable kit for producing an endothelialized graft using microvascular endothelial cells harvested from the patient who is to receive that graft. The subject kit is designed to isolate endothelial cells from human fat, to process that fat to produce a cell deposition product, and to deposit that product on the surface of a graft, all under sterile conditions established and maintained within the components of the kit. The kit is a closed system which lessens the likelihood of contamination and reduces the amount of labor required and user error.

Accordingly, a primary object of the present invention is the provision of a kit for producing endothelialized grafts for implantation in humans.

Another object of the present invention is the provision of a system which establishes and maintains sterility of harvested autologous endothelial cells during processing procedures required to produce the implantable endothelialized vascular graft.

These and other objects of the present invention will become apparent from the following, more detailed description and is illustrated in its specific embodiment in the accompanying drawings.

BRIEF DESCRIPTION OF THE DRAWINGS

FIG. 7(a) is an enlarged front view of the endothelial cell isolation device of FIG. 2;

FIG. 7(b) is an enlarged side view of the endothelial cell isolation device of FIG. 2;

FIG. 10 is a greatly enlarged side view of the components of the inner process tube of FIG. 9;

FIG. 11 is a greatly enlarged side view of the components of the outer process tube of FIG. 9;

DETAILED DESCRIPTION OF THE INVENTION

In accordance with the preferred methods of the present invention, subcutaneous fat is removed from the patient using modified liposuction techniques and transferred to a self-contained, closed device where the fat can be stored under sterile conditions until needed. The fat is sterilely transferred to a digestion device where it is automatically washed initially to remove red blood cells and other debris, followed by a controlled collagenase digestion for 20 minutes at 37° C. The fat slurry is then transferred to an endothelial cell isolation device, again under sterile conditions, where endothelial cells sediment into an isolation device, allowing automatic retrieval of the isolated endothelial cells. The cell suspension is then sterilely transferred to a processing unit wherein the cells are rapidly filtered onto the graft surface under sterile conditions. The endothelial cell isolation and deposition process requires only about 40 minutes for completion using the kit described herein. Following an incubation period, the graft is ready for implantation into the patient. In paired comparisons between the kit and the methods practiced previously, equivalence and reproducibility in the number of isolated endothelial cells and adherence of the cells to graft surface have been observed. The system yields endothelial cell product in numbers acceptable for subsequent high density seeding (range $5.14 \times 10^6$ to $4.24 \times 10^7$ cells from 50 ccs of fat) and adherence to the graft surface. The kit deposits cells along the entire length and diameter of the graft consistently, with no significant difference in cell concentration as compared by analysis of variance. Significant advantages of the kit include 1) closed, sterile fluid path; 2) minimal user input; 3) compatibility with an operating room environment; 4) optimization of the conditions to a highly reproducible process from patient to patient.

Figure 1:
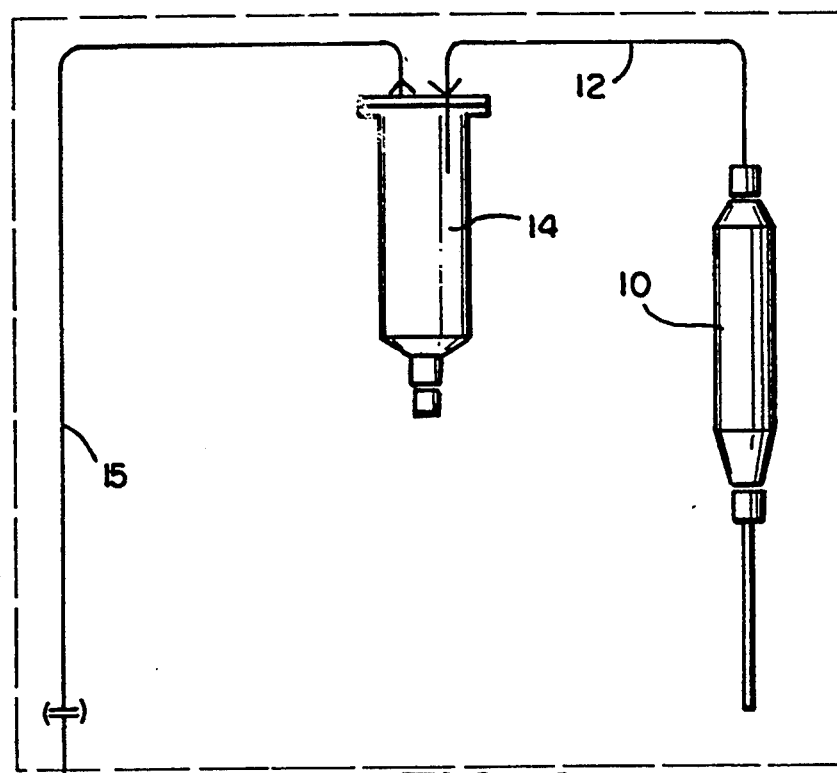
FIG. 1 is a schematic of the fat collection unit which is used to collect fat containing microvascular endothelial cells from the patient to receive the graft, which fat is ultimately collected into a fat collection device.
Figure 3:
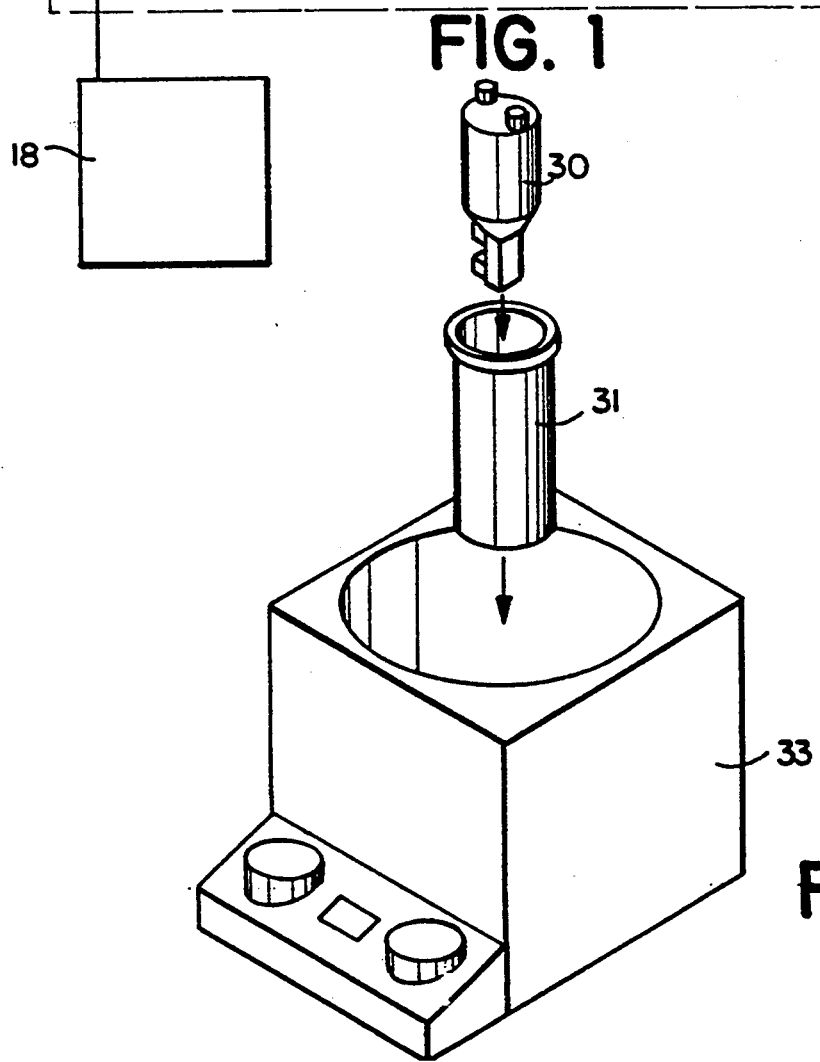
FIG. 3 is a diagram of the endothelial cell isolation unit.
Figure 2:
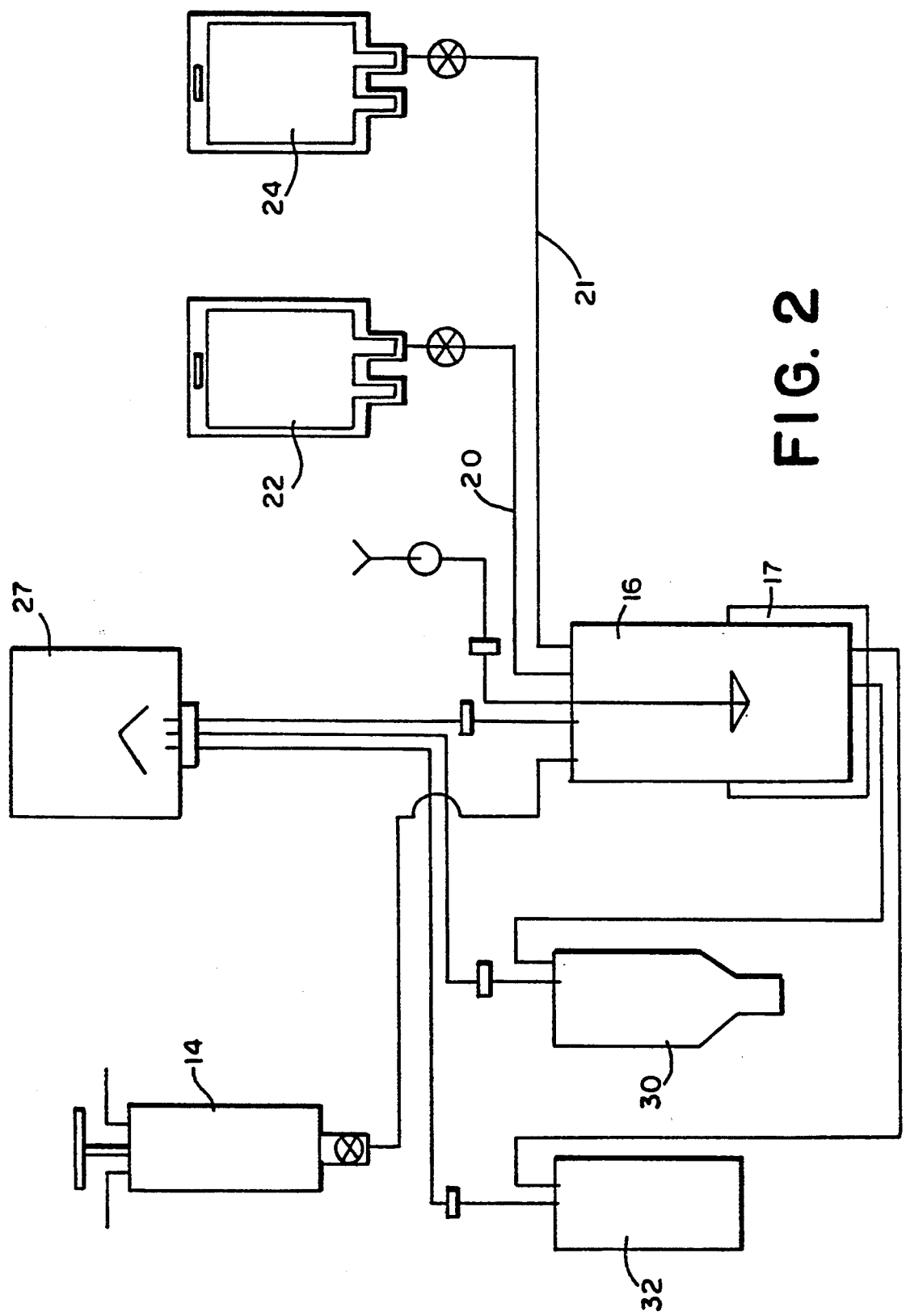
FIG. 2 is a schematic of the digestion unit, wherein the digestion device is shown in association with the fat collection device of the fat collection unit of FIG. 1, which unit is used to produce a digestion product which is transferred to the endothelial cell isolation device, also shown in FIG. 2.
Figure 4:
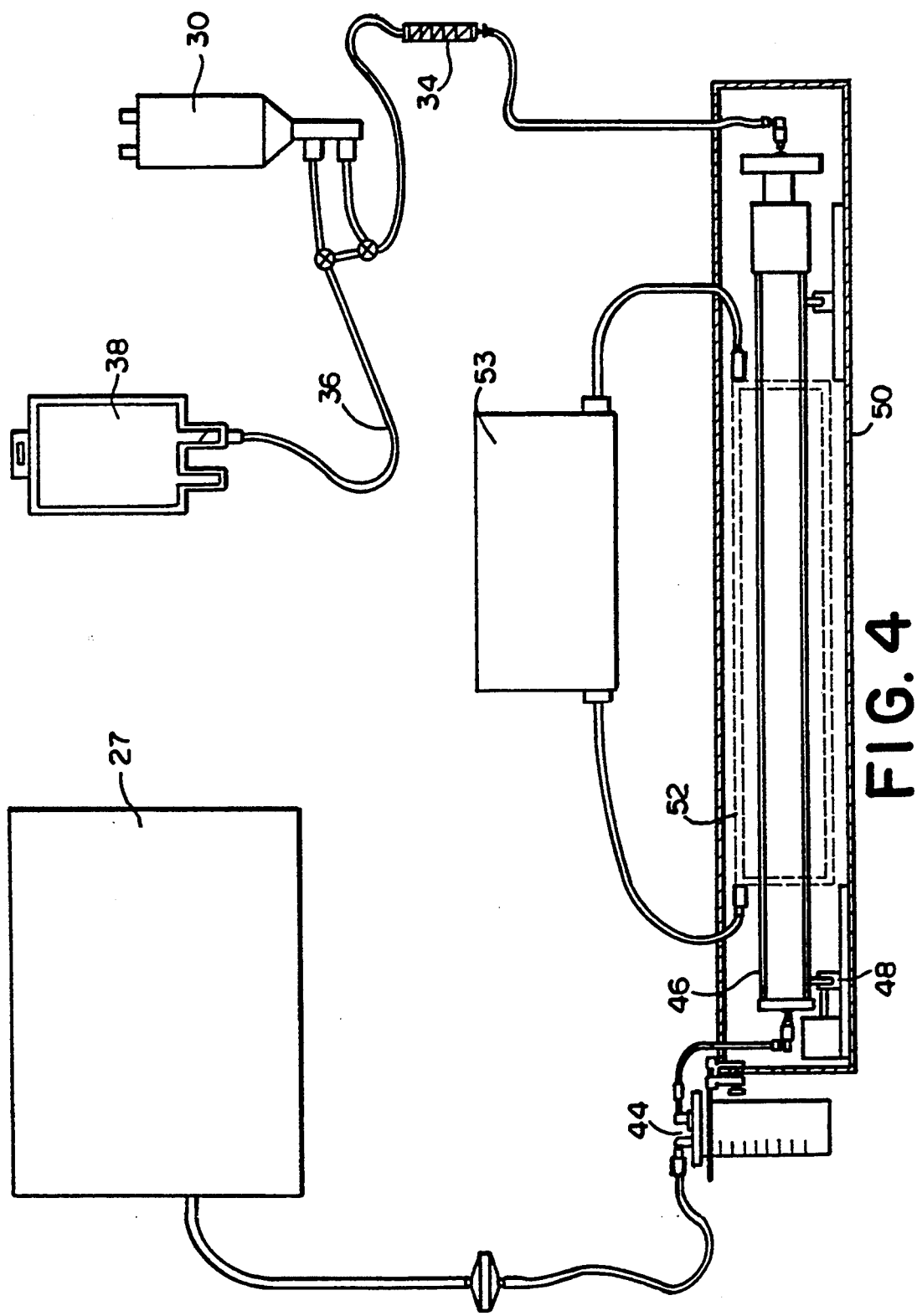
FIG. 4 is a diagram of the vascular graft processing unit and the endothelial cell deposition unit illustrating the components which produce the endothelial cell product and which transfer that product for deposition on a vascular graft.

The system consists of five primary subsystems: 1) fat collection unit (see FIG. 1); 2) digestion unit (see FIG. 2); 3) endothelial cell isolation unit (see FIG. 3); 4) vascular graft processing unit (see FIG. 4); and 5) endothelial cell deposition unit (see FIG. 4).

The fat collection unit (FIG. 1) collects subcutaneous fat tissue sample from a patient. The components include: in-flow tubing (12), fat collection device (14), vacuum tubing (15), aspiration cannula (10) and an aspiration pump (15). The aspiration pump (15) is used to suction subcutaneous fat tissue from the patient through the cannula (10) and in-flow tubing (12) and into the fat collection device (14).

Figure 5:
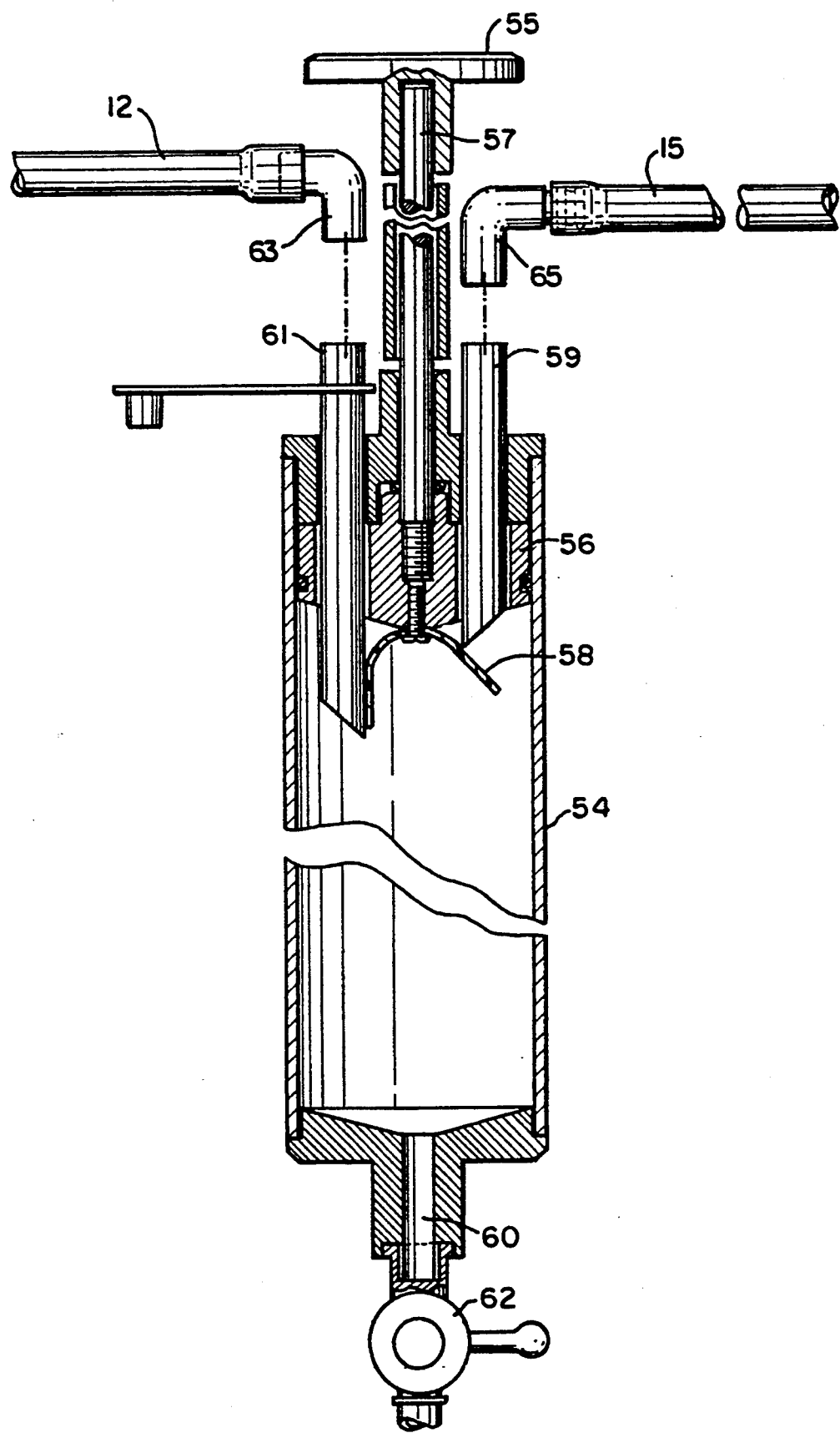
FIG. 5 is a cross-section, on a greatly enlarged scale, of the fat collection device of FIG. 1.

The fat collection device is shown in FIG. 5. It consists of a cylindrical chamber (54) with two vacuum line ports at the top (59 and 61) and an outlet port (60) at the bottom connected to a two-way stopcock (62) A plunger rod (57) passes through the top of the chamber and is connected to a syringe-like stopper (56). The stopper has two holes through which vacuum line ports (59 and 61) pass. When the plunger is in the "down" position, a flexible rubber diaphragm (58) covers the bottom of the stopper and the holes. When the plunger is in the "up" position, the rubber diaphragm (58) is pushed away from the bottom of the stopper by the vacuum line ports (59 and 61) thus opening communication between the inside of the chamber and the vacuum lines (12 and 15). In order to use the device, it must be placed in line with the vacuum line of a liposuction system by using the elbow connectors (63 and 65) In addition, the plunger rod must be in the "up" position. During liposuction, the device acts as a catch trap for the fat tissue. After the appropriate amount of fat is collected, the vacuum line elbow connectors (63 and 65) are disconnected and the plunger rod (57) is pushed down. The rubber diaphragm (58) assumes its original position covering and sealing the bottom of the stopper as it forces the fat tissue out of the outlet port. The subject device serves two functions: to collect fat and facilitate transfer to the digestion unit in a sterile manner.

The digestion unit (FIG. 2) rinses the fat tissue sample with rinse solution and digests it with the enzyme collagenase. The components include: digestion device (16), waste vessel (32) endothelial cell isolation device (30), digestion stand (17), collagenase solution IV bags/sets (20 and 22), rinse solution IV bags/sets (21 and 24) control box (27) for temperature and fluid transfer controls and system vacuum source, assorted tubing connectors, air filters, valves. The fat tissue is manually transferred from the fat collection device (14) through a closed line into the digestion device (16). The fat tissue is rinsed therein with rinse solution introduced into the chamber from the rinse solution IV bags/sets (21 and 24). The rinse solution is drained from the chamber into the waste vessel (32) after rinsing is completed. The collagenase solution is then transferred from the collagenase solution IV bags/sets (20 and 22) into the digestion device (16). Digestion of the fat tissue by the collagenase solution occurs while the mixture is agitated with filtered air and heated to 37° C. The digested fat tissue and collagenase solution mixture is then vacuum transferred into the endothelial cell isolation device (30) for further processing.

Figure 6A:
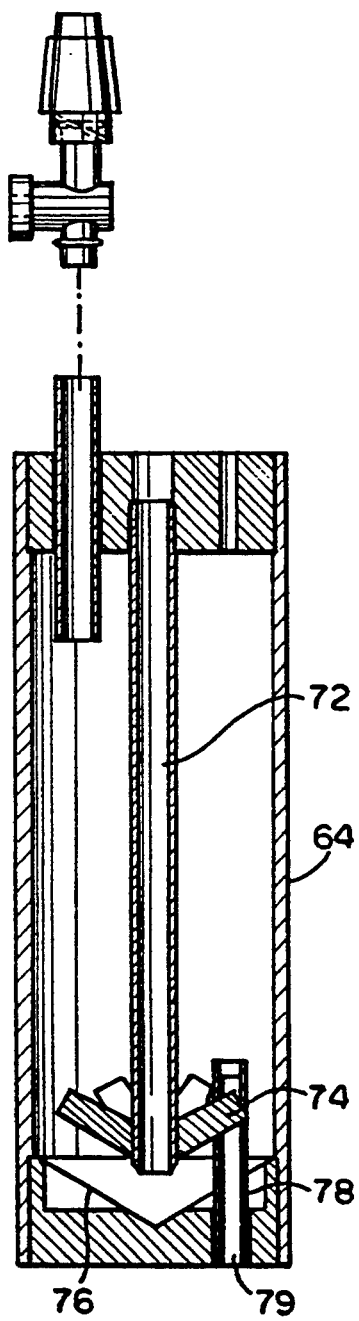
FIG. 6(a) is a longitudinal cross-section, in a greatly enlarged scale, of the digestion device of FIG. 2.
Figure 6B:
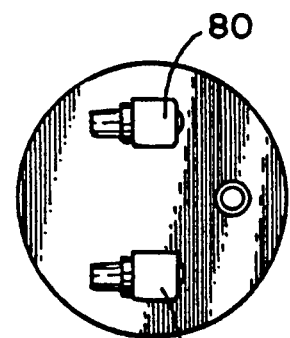
FIG. 6(b) is a bottom view, in a greatly enlarged scale, of the digestion device of FIG. 2.
Figure 6C:
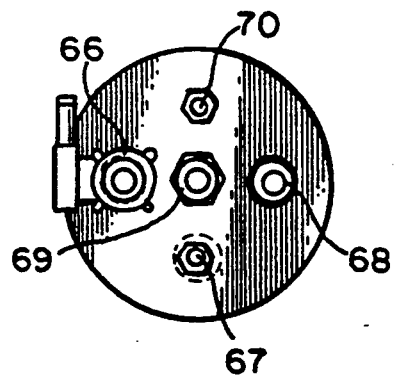
FIG. 6(c) is a top end view, in a greatly enlarged scale of the digestion device of FIG. 2.

The digestion device is shown in FIG. 6. It consists of a chamber (64) with several inlet ports at the top (66, 67, 68, 69 and 70) one of which contains a filter and is connected to a tube (72) which terminates near the bottom of the chamber. A series of "fingers" (74) is bonded to the end of the tube in a radial fashion. At the bottom of the chamber is a conical mesh filter (76) below which are two outlet ports (80 and 82) and a temperature probe sheath (78). During use, the collected fat tissue is introduced into the chamber (64) through one of the top inlet ports (66) followed by rinse solution (Media 199E, flanks, saline, PBS or other physiological buffered solution) through another of the inlet ports (67). A vacuum line, connected to another inlet port (68) causes filtered air to enter through the center port (69) and tube (72) which air bubbles up through the fat mixture creating agitation. The "fingers" (74) serve to distribute the bubbling air to ensure uniform agitation and provide a frictional surface to facilitate break-up of the fat. The rinse solution is then drawn out through the bottom of the mesh and expelled through one of the outlet ports (80) leaving behind fat tissue relatively free of blood. Digestive enzyme solution (collagenase, dispase, trypsin, or other tissue dissociation enzyme) is introduced through another of the top inlet ports (70) followed by agitation by bubbling. Throughout this process, a temperature probe (79) inside the probe sheath (78) monitors the process temperature and sends feedback to an external heat controller within the control box (27). When digestion is complete, the digested fat solution, rich in microvessel endothelial cells, is drawn out through the bottom mesh and expelled through an outlet port (82) for subsequent processing. The mesh (76) retains undigested tissue and large fibrous matter which is discarded with the device. The subject device is a closed system which lessens the likelihood of contamination and reduces the amount of labor and user error.

The endothelial cell isolation unit (shown in FIG. 3) separates and isolates the endothelial cells from within the digested fat tissue sample. The components include: centrifuge (33), centrifuge shields (31), endothelial cell isolation device (30). The endothelial cell isolation device (30) is placed into a centrifuge shield and the assembly is placed into the centrifuge (33). Centrifugation isolates the endothelial cells. The endothelial cell isolation device (30) is then placed in line with the vascular graft processing unit and mounted on the endothelial cell deposition unit.

The endothelial cell isolation device is shown in FIG. 7. It consists of a primary chamber (88) tapering to a secondary chamber or ampule (90) having inlet and outlet ports (92 and 94) In line with each port (92 and 94) is a two-position valve (91 and 93). The first position allows communication between the primary and secondary chambers. The second position allows communication between the secondary chamber and the outside port. Each valve (91 and 93) is initially turned to the first position. Digested fat tissue is introduced through the top port (84) The device is then placed into a centrifuge and spun. Centrifugation separates endothelial cells into the ampule (90) the dimensions of which are optimized for isolating a "pellet" of endothelial cells between the two ports. The valves are then turned to the second position isolating the "pellet" from the primary chamber (88) above and packed red blood cells below. The endothelial cell "pellet" may then be flushed out by attaching a pressurized line to the inlet port (92) or vacuum line to the outlet port (94). The subject device is a closed system which maintains sterility and reduces the amount of labor and user error.

The vascular graft processing unit shown in FIG. 4 protects, maintains sterility and facilitates the processing of the graft during handling, pre-wetting and cell deposition. The components include: process tube assembly including an inner and an outer tube (46), graft, vacuum line/trap assembly (44), vortex/mesh assembly (34), autologous serum/media solution IV bags/sets (36 and 38). The graft is mounted within the inner tube of the process tube assembly. The purpose of the outer tube is to maintain sterility of the inner tube. The graft is pre-wetted prior to cell deposition by drawing the autologous serum/media solution from an IV bag, through the vortex/mesh assembly, into the lumen of the graft, and out through the graft wall until all air is purged from the inner tube of the process tube assembly. The graft processing unit is then transferred to the endothelial cell deposition unit.

Figure 8:
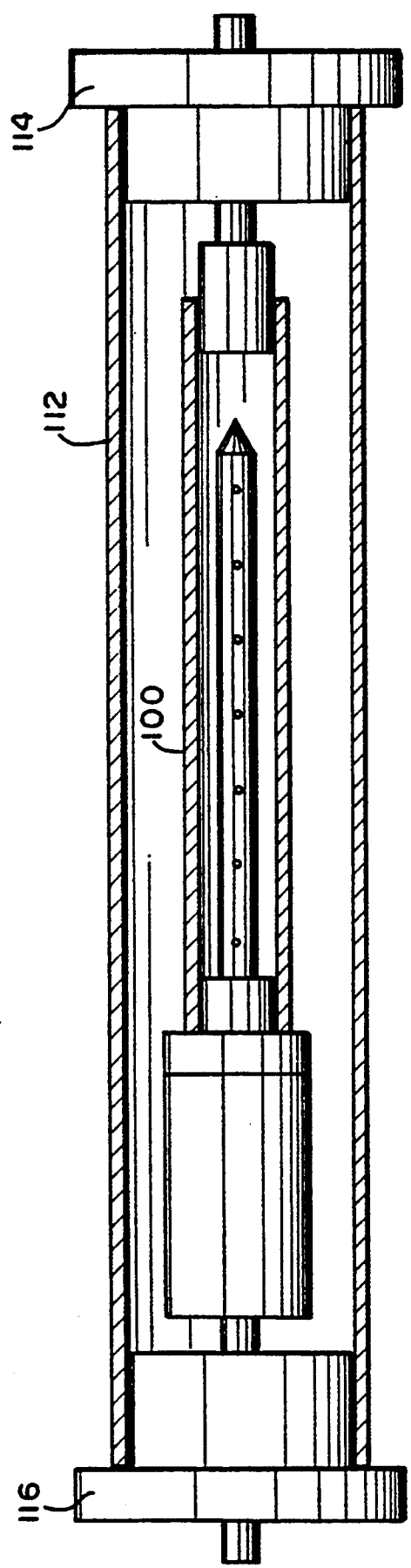
FIG. 8 is a diagrammatic cross section of the process tube assembly, shown in FIG. 4 within the endothelial cell deposition unit, which process tube assembly is used to introduce the endothelial cell product onto the interior surface of the graft lumen.
Figure 9:
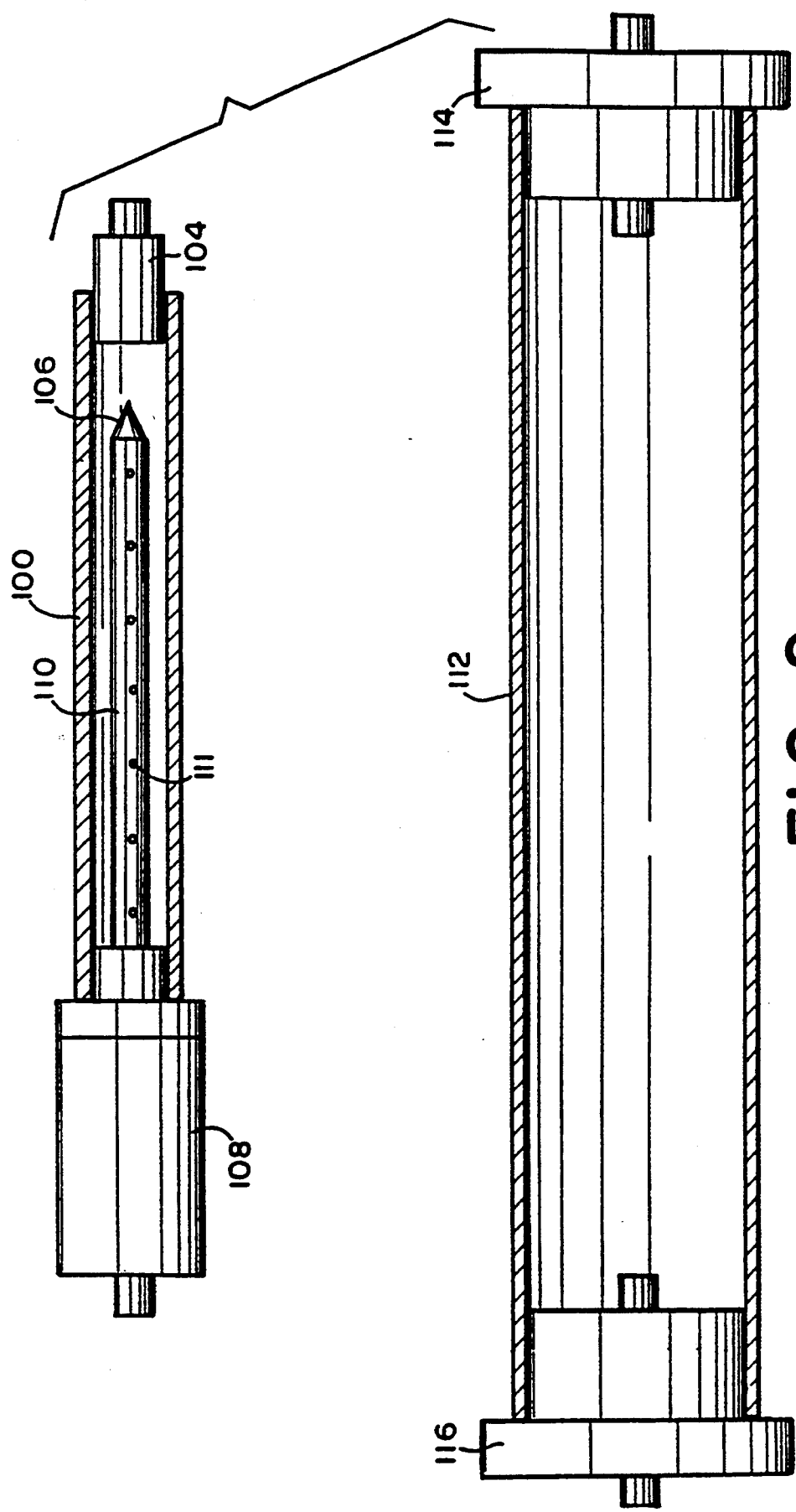
FIG. 9 is an enlarged diagrammatic cross-section of the inner and outer process tubes of the vascular graft processing unit illustrated in FIG. 8.

The fully assembled process tube is shown in FIG. 8. It consists of two major assemblies: inner process tube (100) and outer process tube (112) (see FIG. 9). As shown in FIG. 10, the inner process tube consists of the following sub-assemblies: vent cap (104), handle cap (108), inner process tube body (102), tunneler (110), tunneler tip (106). A graft is threaded through the lumen of the tunneler (110) and is attached to the handle cap (108) prior to assembly. As shown in FIG. 11, the outer process tube consists of the following subassemblies: outer process tube body (113), inflow endcap (116), outflow endcap (114). In its fully assembled form, the process tube assembly serves the following functions: it houses, protects and maintains sterility of the graft during shipment and handling in the operating room; it supports the graft and allows fluid access to the graft lumen during endothelialization; it breaks down into a sub-assembly which facilitates implantation of the graft while protecting the endothelial lining. During endothelialization, the inflow endcap of the device (116) is connected to a container of endothelial cell suspension, and the outflow endcap (114) is connected to a vacuum source in the control box (27). Negative pressure external to the porous graft causes the endothelial cell suspension to flow into the graft lumen and out through the wall thereby filtering endothelial cells onto the inner graft wall. The filtered solution continues to flow out through the holes (111) in the tunneler wall (110) and out of the vent cap (104). During this operation, the device may be rotated about its central axis by the addition of rotary fittings at the outer process tube end caps. After endothelialization is complete, the inner process tube (100) is removed from the outer process tube (112) and the handle cap (108)/tunneler (110)/tip (106) assembly is removed from the inner process tube body (102) The graft may then be "tunneled" through, for example, the patient's leg tissue for proper graft placement without contacting or disturbing the graft. Once positioned, the handle cap (108) is detached from the tunneler (110) and the tunneler (110) is withdrawn, leaving the graft in place for the distal anastomosis. An IV line containing autologous serum media solution may be connected to the handle cap (108) to maintain wetting of the graft lumen during surgical placement. When the distal anastomosis is completed, the graft is snipped at the proximal end, releasing it from the handle cap (108) and readying it for the proximal anastomosis.

One embodiment of the endothelial cell deposition unit shown in FIG. 4 promotes endothelial cell deposition onto the lumen of the graft. The components include: process tube rotation fixture (48) insulated trough (50) heating pad (52) water circulator/heater (53) The process tube assembly (46) is positioned on the rotation fixture within the insulated trough and wrapped in the heating pad which is heated by the water circulator. The cell deposition procedure is initiated by using vacuum to draw autologous serum/media solution and the isolated endothelial cells from endothelial cell isolation device (30) The endothelial cells and autologous serum/media solution pass through the vortex/mesh assembly (34) which breaks up the endothelial cell pellet and filters out gross particulate. The endothelial cells resuspended in the solution are pressurized into the lumen of the graft under a 2.5 to 5.0 psi vacuum at a flow rate of approximately 100 cc/minute. The graft filters the solution leaving endothelial cells on the luminal wall.

During pressurization, and subsequent cell-graft association, the graft is rotated about its central axis at a constant rate and maintained at 37° C.

Ancillary items include: blood collection bag and transfer bag without anticoagulant to be used for blood collection and serum separation, the serum to be used for the make-up of autologous serum/media solution and an additional solution IV bag filled with autologous serum/media solution and an administration set to be used to maintain the cells during graft implantation.

Figure 14:
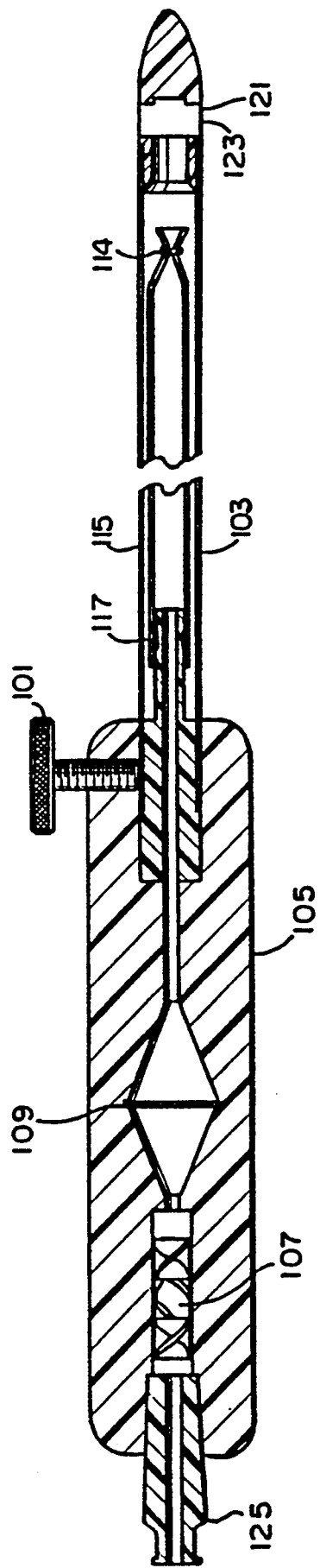
FIG. 14 is a longitudinal cross-section, in a greatly enlarged scale, of the preferred embodiment of the endothelial cell deposition device.

In another, preferred embodiment, shown in FIG. 14, the outer process tube, the inner process tube body, and vent cap have been eliminated. As shown in FIG. 14, a thumbscrew (101) secures the tunneler (103) to the handle (105). The vortex/mesh assembly is incorporated within the handle (105). The porous graft (115) is shown within the tunneler (103). The proximal end of the graft (115) is secured to the outflow end (117) of the handle (105). The distal end of the graft is tied off (119). A pointed tip (121) and vent hole (123) are located at the distal end of the tunneler (103). During endothelialization, the inflow end (125) of the handle (105) is connected to a fluid source containing a pellet of endothelial cells. The fluid is forced under pressure through the vortex (107) and mesh (109) to break up the pellet of endothelial cells and filter out any large particulates. The endothelial cell suspension flows into the graft lumen and out through the porous wall of the graft (115). Endothelial cells are thereby filtered onto the inner graft wall. The filtered solution continues to flow out through the graft/tunneler annular space and the vent hole (123). After an appropriate incubation period, the graft may be "tunneled" through, for example, the patient's leg tissue for proper graft placement without contacting or disturbing the graft. Once positioned, the handle (105) is detached from the tunneler (103) by acting on the thumbscrew (101) and the tunneler (103) is withdrawn, leaving the graft in place for the distal anastomosis. An intravenous (IV) line containing autologous serum media solution may be connected to the inflow end (125) of the handle (105) to maintain wetting of the graft lumen during surgical placement. When the distal anastomosis is completed, the graft is snipped at the proximal end (117), releasing it from the handle (105) and readying it for the proximal anastomosis.

The invention is further illustrated by means of the following examples. These examples are meant to be illustrations only and are not intended to limit the present invention to these specific embodiments.

EXAMPLE 1

Figure 12:
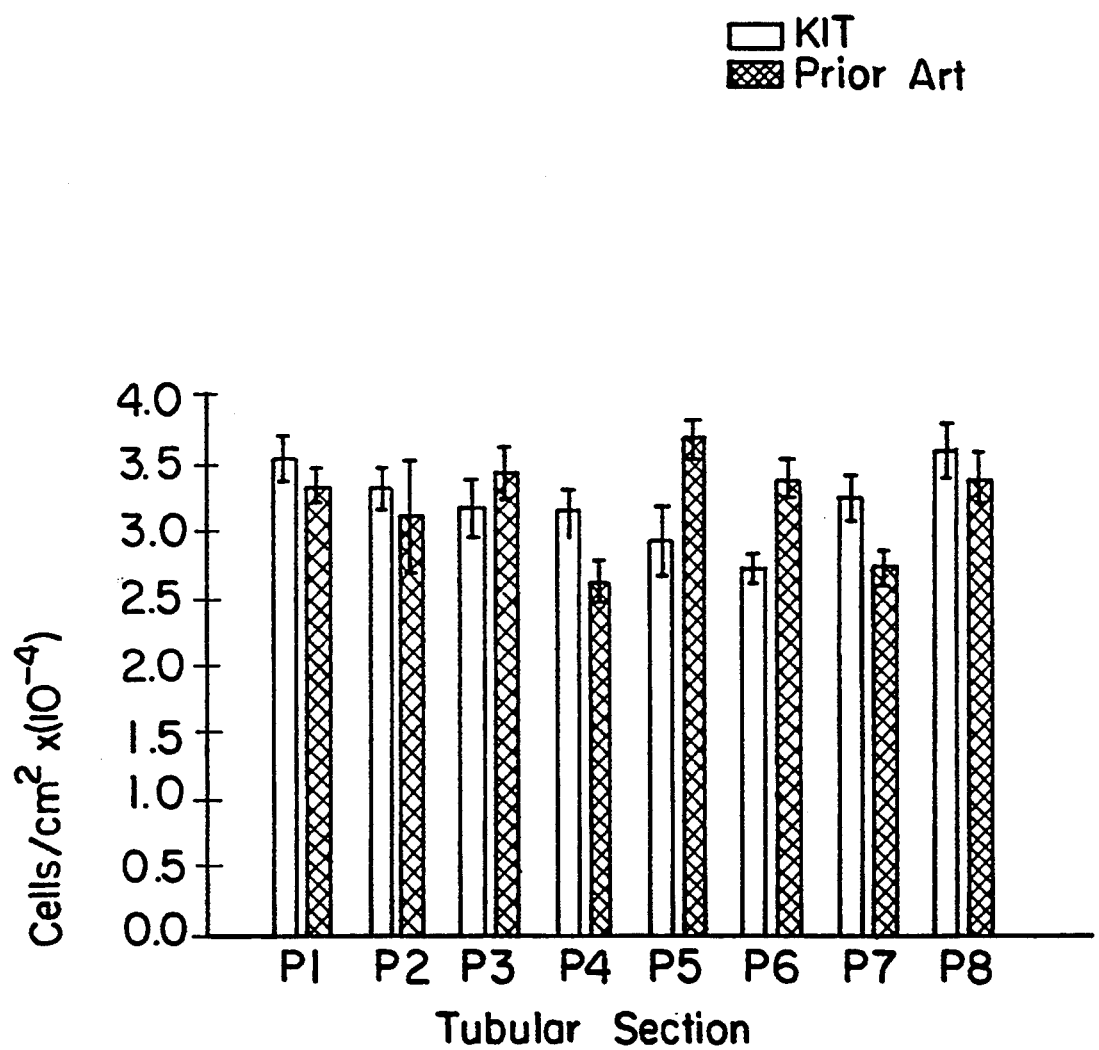
FIG. 12 is a bar graph showing the average endothelial cell density achieved per section of processed graft for the grafts processed using the preferred kit of the present invention and those using prior art methods.

Microvascular endothelial cells were isolated and deposited on 4 mm×80 cm expanded polytetrafluoroethylene (ePTFE) grafts using both the kit and patented methods. After a two hour rotation, the grafts were rinsed with media and cut into 8 sections. PI is where the cells were introduced and PS is the opposite end. The graft segments were hematoxylin stained and the cells counted using an automated image analysis system. FIG. 12 provides the average cell density achieved per section on such Gore-Tex ® tubular grafts.

EXAMPLE 2

Figure 13:
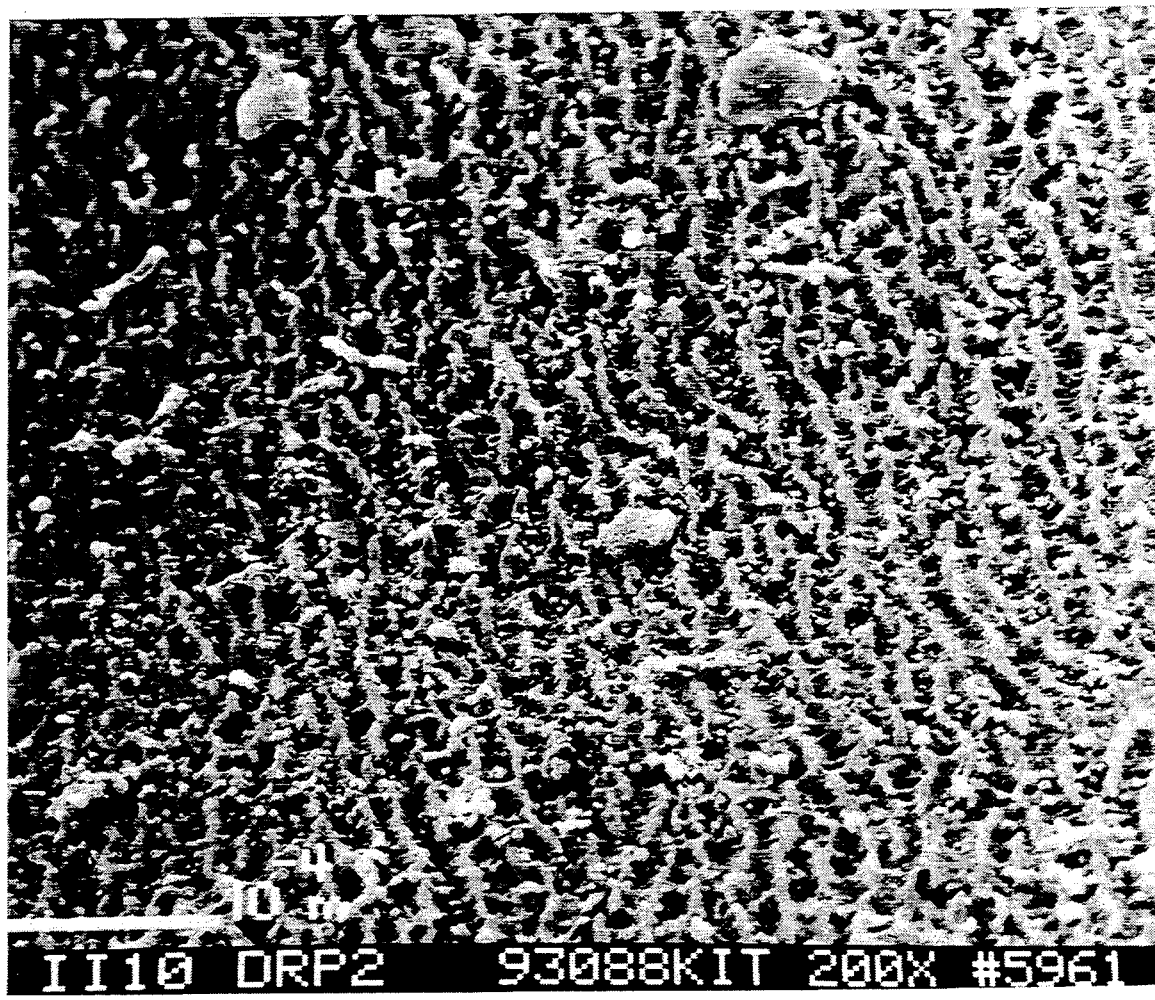
FIG. 13 is a scanning electron micrograph of a graft processed with the preferred kit of the present invention.

Endothelial cell product was prepared and deposited on an ePTFE graft using the kit. A scanning electron micrograph of the microvascular endothelial cells deposited on the graft is shown in FIG. 13. The endothelial cell product was consistently deposited along the entire length of the graft with no significant variation in cell concentration.

As seen from the above a simple, reliable kit for producing an endothelialized graft using microvascular endothelial cells is provided. These cells are harvested from a patient who is to receive the graft and processed through the use of kit which isolates those cells to produce cell deposition product, and deposits that product on the surface of a graft, all under sterile conditions established and maintained within the components of the kit.

While the foregoing description has been directed to the preferred embodiment kit of the present invention, those of ordinary skill in the art in this field will appreciate that various modifications can be made in the materials and methods described herein without departing from the scope of the present invention, which is defined more particularly in the claims appended hereto.

What is claimed:

1. A cell product deposition device for retaining a graft and directing cell product into the graft for deposition on the graft comprising:

a tunneler tube means for housing and supporting the graft, wherein the tunneler tube means comprises a tunneler tube lumen and the graft is disposed within the tunneler tube lumen, and wherein the tunneler tube means comprises at least one aperture; and a handle means detachably connected to said tunneler tube means comprising a handle lumen in fluid communication with a graft lumen of said graft and a source of cell product, whereby cell product is introduced into said graft lumen through said handle means and flows through the graft and through said at least one aperture.

2. The cell product deposition device of claim 1 wherein said housing and supporting means has a pointed tip to facilitate graft placement.

3. The cell product deposition device of claim 1 wherein said housing and supporting means has a means to vent excess endothelial cell product during the endothelial cell product deposition process.

4. The cell product deposition device of claim 1 wherein said tunneler tube means is sufficiently malleable to conform to a patient's tissue to facilitate graft placement and sufficiently rigid to remain stable during graft placement.

5. The cell product deposition device of claim 1 further comprising:
an outer process tube surrounding the tunneler tube and handle for maintaining sterility during the cell deposition process.

6. Apparatus for depositing cell product in a graft and inserting the graft in a vessel comprising:
a tunneler tube comprising:
a hollow portion for supporting a graft, the graft disposed within a lumen of the hollow portion,
at least one aperture, and
a pointed end cap attached to a distal end of the tunneler tube; and
a handle connected to the graft and releaseably connected to a proximal end of the tunneler tube comprising: an inlet in fluid communication with a source of cell product and outlet in fluid communication with a lumen of the graft,
whereby, during deposition, the cell product flows through the handle means, into the graft and exits through the aperture, and, during insertion, the tunneler tube is manipulated by the handle to enter a vessel and is then released from the handle and removed to accommodate anastomoses.

7. The apparatus of claim 6, wherein the at least one aperture are disposed adjacent the pointed end cap.

8. The apparatus of claim 6, wherein the at least one aperture comprises comprise a plurality of apertures spaced along the hollow portion of the tunneler tube.

9. The cell product deposition device of claim 1, wherein said handle means comprises a filtering and dispersion means in fluid communication with the handle lumen for filtering out large tissue particles and dispersing the cell product prior to its being deposited on said graft.

10. The cell product deposition device of claim 1, wherein said handle is secured to said tunneler tube means by a screwing means.

* * * * *